United States Patent [19]
Carothers et al.

[11] Patent Number: 5,398,672
[45] Date of Patent: Mar. 21, 1995

[54] METHOD FOR SELF-EXAMINATION OF THE INNER THROAT SUCH AS THE VOCAL CORDS

[76] Inventors: Patrice O. Carothers, 378 Hickory Hill, Chagrin Falls, Ohio 44022; Robert L. Katz, 22099 Parnell Rd., Shaker Heights, Ohio 44122

[21] Appl. No.: 266,328

[22] Filed: Jun. 27, 1994

Related U.S. Application Data

[63] Continuation of Ser. No. 952,075, Sep. 25, 1992, abandoned.

[51] Int. Cl.6 .............................................. A61B 1/06
[52] U.S. Cl. ...................................... 128/22; 128/11; 128/898; 359/879; 362/138
[58] Field of Search .......................................... 128/898

[56] References Cited

U.S. PATENT DOCUMENTS

| | | | |
|---|---|---|---|
| 181,312 | 8/1876 | Carrozzi . | |
| 404,021 | 5/1889 | Tice . | |
| 532,666 | 1/1895 | Johnson | 128/23 |
| 1,201,550 | 10/1916 | Brush | 128/11 |
| 1,342,351 | 6/1920 | Roy . | |
| 1,817,417 | 8/1931 | Meitzler | 362/139 X |
| 2,222,879 | 11/1940 | Porter | 362/138 |
| 2,275,304 | 3/1942 | Maurud . | |
| 3,459,178 | 8/1969 | Fleming | 128/22 |
| 4,120,228 | 10/1978 | Windows, Jr. | 84/453 |
| 4,354,835 | 10/1982 | Lewis | 433/30 |
| 4,658,697 | 4/1987 | Wean | 84/465 |
| 4,947,896 | 8/1990 | Bartlett | 128/11 |

FOREIGN PATENT DOCUMENTS

| | | | |
|---|---|---|---|
| 0224896 | 6/1987 | European Pat. Off. | 433/30 |
| 2380763 | 10/1978 | France . | |
| 480692 | 3/1953 | Italy | 362/138 |

OTHER PUBLICATIONS

American Optical Co., "The Laryngoscope", 1941, pp. 6, 10–14.
Curvelite Products Medical Catalog, 1939, p. 5.
"Medical–Surgical Review", p. 18 (halogen lamp).

*Primary Examiner*—Richard J. Apley
*Assistant Examiner*—Donna L. Maraglio
*Attorney, Agent, or Firm*—Rankin, Hill, Lewis & Clark

[57] ABSTRACT

A kit for self-examination of a person's inner throat such as the vocal cords, comprising a first mirror and a second mirror, a light source, and means for positioning the person's tongue to access visualization of their inner throat; the first mirror being supported on a stand, the second mirror being sized for insertion into the person's mouth and positionable for observation of the person's vocal cords, the light source being positionable to illuminate the person's inner throat so that an image of the person's vocal cords can be reflected from the second mirror to the first mirror for observation by the person.

1 Claim, 1 Drawing Sheet

METHOD FOR SELF-EXAMINATION OF THE INNER THROAT SUCH AS THE VOCAL CORDS

This is a continuation of application Ser. No. 07/952,075, filed on Sep. 25, 1992, now abandoned.

BACKGROUND OF THE INVENTION

The invention relates to apparatus and methods for self-examination of the human anatomy.

Individuals have often exhibited an interest in self-examination and self-diagnosis of observable conditions of their anatomy, particularly for conditions that are afflicted by common ailments. Such self-examination includes examination of the skin, mouth, teeth, scalp and so forth. This interest in self-examination and diagnosis is becoming all the more popular with the growing concern of diseases and ailments that frequently occur between annual physical examinations. As persons become more educated and aware of ailments that may have causes not easily identifiable, self-examination as a preventative measure can be expected to increase, resulting in early intervention and remedial care.

In addition to self-examination for preventative health care, professional entertainers, speakers, singers and the like often have an interest in frequently knowing the condition of their inner throats including the pharynx, larynx, and especially their vocal cords, without the need to arrange for a professional examination. For example, the vocal cords can develop thickening or swelling that could lead to nodules or other mass lesions that may adversely affect use of the vocal cords. Again, such knowledge obtained from self-examination can be beneficial in preventing excessive use of the vocal cords when a harmful condition exists, in addition to early intervention for medical treatment. Speech therapists and other speech professionals also need to be able to provide their clients with a training and educational tool that can assist the client with home practice and observing their inner throats, such as clients with vocal cord abnormalities.

Although apparatus are available for general examination of the mouth, lips and teeth, such apparatus are unsuitable for self-examination of the inner throat, and especially the vocal cords. The need exists, therefore, for a simple and low cost apparatus and method for self-examination of the inner throat and vocal cords.

SUMMARY OF THE INVENTION

The present invention contemplates kit apparatus and a method for self-examination of a person's inner throat, and especially the vocal cords. Such a kit comprises in a preferred embodiment a first mirror and a second mirror, a light source and means for positioning the person's tongue to access visualization of the inner throat, the first mirror being supported on a stand and the second mirror being insertable into the person's mouth and positionable above the person's vocal cords, the light being positionable to illuminate the person's vocal cords so that an image of the vocal cords can be reflected from the second mirror to the first mirror for observation by the person. The invention further contemplates the methods embodied by use of such an apparatus.

These and other aspects and advantages of the present invention will be readily understood and appreciated by those of ordinary skill and knowledge from the following description of the preferred embodiment in the best mode known for practicing the invention, in view of the accompanying drawings.

DETAILED DESCRIPTION OF THE PREFERRED EMBODIMENTS

Figure 1:
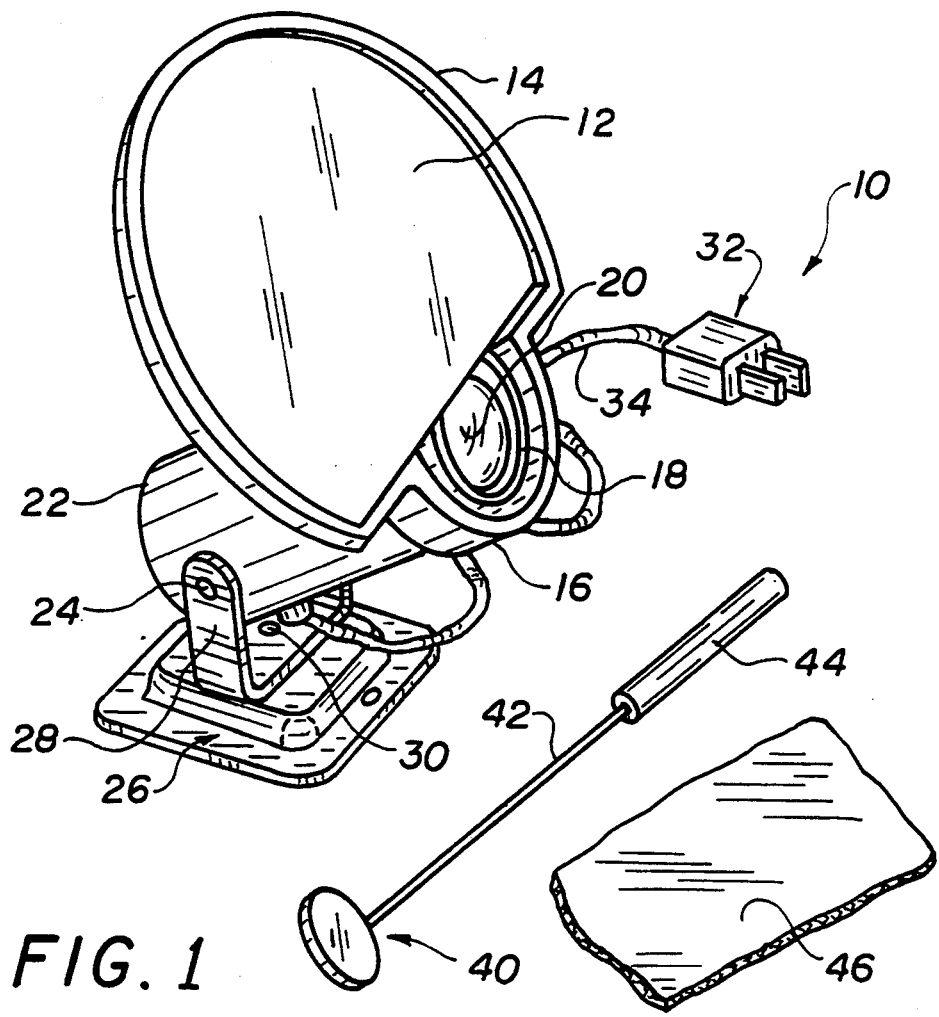
FIG. 1 is a schematic perspective of a kit for self-examination of a person's inner throat in accordance with the invention.

With reference to FIG. 1, a kit apparatus for self-examination of a person's inner throat, including the person's pharynx, larynx and particularly the person's vocal cords, is generally indicated by the numeral 10. The kit includes a first mirror 12 secured in a frame member 14. The mirror is preferably flat, however, a magnifying mirror could be used. The frame 14 preferably includes a partially cylindrical extension 16 that snugly receives one end of a lamp socket 18. A light source or lamp 20 can be screwed into the socket 18 in a conventional manner. We have found that a halogen lamp provides the best light source for the mirror/socket configuration of FIG. 1. The halogen lamp provides a high intensity well defined beam of light that can be directed at the user's mouth and throat.

At an opposite end 22 of the socket 18, the socket and mirror assembly can be pivotally mounted as at 24 on a base or stand 26. As illustrated in FIG. 1, the stand 26 includes a U-shaped bracket 28 that is pivotally connected to the lamp socket. If desired, additional freedom of movement can be provided by attaching the bracket 28 to the base 26 by a pin 30, thus allowing the bracket to be rotated clockwise or counterclockwise to suit the user.

The frame 14 may be made of a rubber or plastic-like material so that it can be easily removed from the socket yet snugly mounted thereon. This permits convenient disassembly of the apparatus 10 for portability. The socket is preferably made of metal or other suitable material that will not be affected by heat generated by the lamp 20. A conventional power plug 32 and power cord 34 can be used to connect the lamp socket to a conventional wall outlet. Of course, a battery operated light could alternatively be used.

The kit 10 further includes a second mirror 40, which preferably is a flat dental examination type mirror. The mirror 40 is attached to a handle 42 that may conveniently include a grip portion 44. The mirror 40 is suitably sized for easy insertion into the person's mouth and throat, with the handle being at least long enough to position the mirror for observation of the user's vocal cords.

The kit also includes a supply of gauze 46. The gauze provides a simple, effective and sanitary way for the user to grip, with only one hand, the end of their tongue in order to extend and lower the tongue in such a manner as to access visualization of the vocal cords for self-examination using the mirrors 40, 12.

Figure 2:
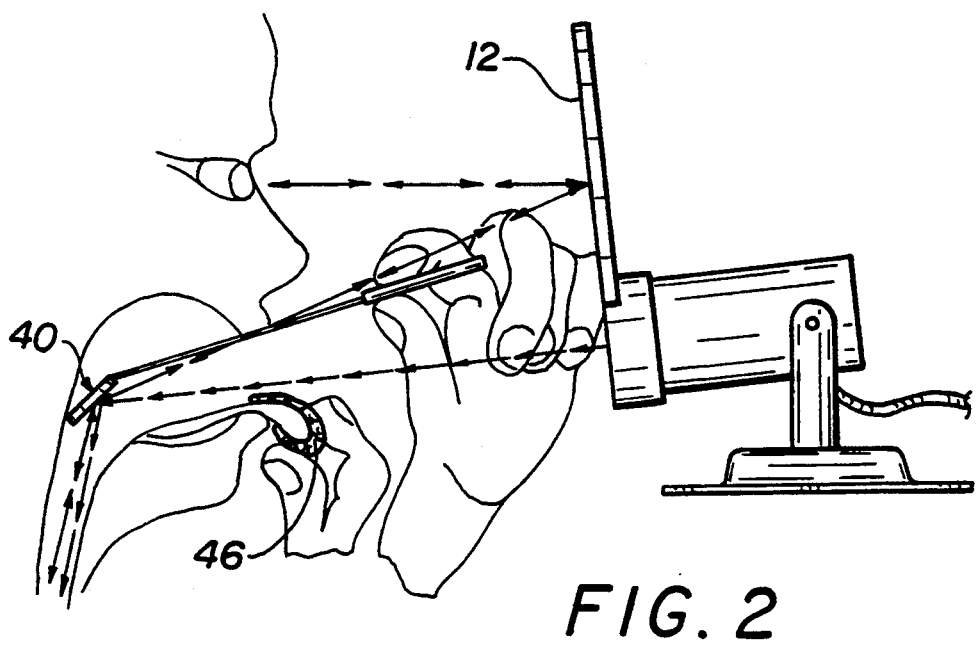
FIG. 2 is a simplified representation of the invention in the manner it can be used for self-examination.

With reference now to FIG. 2, an illustration is provided of how a person can perform a self-examination of that person's inner throat and particularly their vocal cords. As shown, with their one hand the person uses the gauze to grip the end of their tongue and extend it in a downward fashion. This is done with the mirror 12 and light 18 facing the person such that light shines into the mouth and throat to the mirror 40.

Using their other hand, the person can position the small mirror 40 above the person's vocal cords and orient the mirror 40 in such a manner that an image of the vocal cords is reflected back to the large mirror 12 for observation by the user. It has been found that a flat mirror 12 seems to provide the best image for a person to self-examine their inner throat; however, a magnifying mirror can be used. An important aspect and advantage of the present invention is that the gauze permits a sanitary way to position the tongue properly while not interfering with the positioning of the mirror 40 near the vocal cords.

While the invention has been shown and described with respect to specific embodiments thereof, this is for the purpose of illustration rather than limitation, and other variations and modifications of the specific embodiments herein shown and described will be apparent to those of ordinary skill in the art within the intended spirit and scope of the invention as set forth in the appended claims.

What is claimed is:

1. A method for self-examination of a person's vocal cords using a dual mirror apparatus comprising the steps of:

a. having the person position a portable flat observation mirror near the person for visual observation of an image of the vocal cords reflected from the observation mirror, wherein the flat observation mirror is retained in a flexible frame that is slideably attached by the person to a portable plug-in light socket, and that can be slideably removed by the person for improved portability of the apparatus, further wherein the light socket holds a light source to illuminate the person's inner throat and is pivotally attached to a base that supports the socket and mirror/frame when assembled by the person, so that the flexible frame and pivotal attachment allow the person to position the observation mirror non-vertically for optimal viewing of the person's vocal cords;

b. having the person hold in one hand an examination mirror that can be positioned by the person to reflect an image of the person's vocal cords to the observation mirror so that the person can see an image of their vocal cords in the observation mirror; and c. while using the examination mirror having the person hold in their other hand a piece of gauze-like material that is used by the person to grip their tongue and position their tongue so that the person can concurrently use the examination mirror to observe their vocal cords.

* * * * *